(12) United States Patent
Shirota et al.

(10) Patent No.: US 8,803,056 B2
(45) Date of Patent: Aug. 12, 2014

(54) LIGHT SOURCE APPARATUS HAVING A LIGHT EMISSION INTENSITY DETECTION SECTION RECEIVES BOTH OF A LEAK LIGHT AND A LIGHT EMITTED FROM THE LIGHT SOURCE AND REFLECTED BY AN OPTICAL ELEMENT

(71) Applicant: Olympus Medical Systems Corp., Tokyo (JP)

(72) Inventors: Yutaka Shirota, Kawasaki (JP); Tomoya Takahashi, Hachioji (JP); Yusuke Yabe, Chofu (JP); Masato Toda, Hachioji (JP); Koji Omori, Hachioji (JP); Takahiro Masaki, Kawasaki (JP); Daisuke Akiyama, Fuchu (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/973,447

(22) Filed: Aug. 22, 2013

(65) Prior Publication Data

US 2014/0054450 A1    Feb. 27, 2014

Related U.S. Application Data

(63) Continuation of application No. PCT/JP2013/058056, filed on Mar. 21, 2013.

(30) Foreign Application Priority Data

Apr. 4, 2012    (JP) .................................. 2012-085740

(51) Int. Cl.
*G01J 1/32*    (2006.01)
(52) U.S. Cl.
USPC ............................................ 250/205; 250/216
(58) Field of Classification Search
USPC ........ 250/205, 216, 239, 214.1, 458.1, 201.3, 250/306, 307; 600/101, 109, 178, 180, 182, 600/466, 467, 476
See application file for complete search history.

(56) References Cited

U.S. PATENT DOCUMENTS 7,667,211 B2 *    2/2010    Takahashi .................. 250/458.1

FOREIGN PATENT DOCUMENTS

| JP | 11-313797 A | 11/1999 |
|---|---|---|
| JP | 2008-307171 A | 12/2008 |
| JP | 2010-158415 A | 7/2010 |

* cited by examiner

*Primary Examiner* — Que T Le
(74) *Attorney, Agent, or Firm* — Scully, Scott, Murphy & Presser, P.C.

(57) ABSTRACT

A light source apparatus that generates a light to be supplied to an endoscope, which includes: LEDs of respective colors that emit lights; collimator lenses that receive emitted lights and emit the received lights; and illuminance sensors arranged at positions where the illuminance sensors can receive both of leak lights of the lights emitted from the LEDs of respective colors, which are not used as illumination lights, and lights emitted from the LEDs of respective colors and reflected by the collimator lenses.

13 Claims, 10 Drawing Sheets

LIGHT SOURCE APPARATUS HAVING A LIGHT EMISSION INTENSITY DETECTION SECTION RECEIVES BOTH OF A LEAK LIGHT AND A LIGHT EMITTED FROM THE LIGHT SOURCE AND REFLECTED BY AN OPTICAL ELEMENT

CROSS-REFERENCE TO RELATED APPLICATION

This application is a continuation application of PCT/JP2013/058056 filed on Mar. 21, 2013 and claims benefit of Japanese Application No. 2012-085740 filed in Japan on Apr. 4, 2012, the entire contents of which are incorporated herein by this reference.

BACKGROUND OF THE INVENTION

1. Field of the Invention

The present invention relates to a light source apparatus that detects a light emission intensity while generating light to be supplied to an endoscope by a light-emitting element.

2. Description of the Related Art

As a light source apparatus of illumination light to be irradiated from an endoscope to a subject, a xenon lamp or the like has been conventionally used. However, with a spread of an LED, a light source apparatus using a light-emitting element such as an LED has been put into practical use in view of low power consumption and durability.

An LED is a light source which emits a light of a narrower band, compared with the xenon lamp, or the like, which is capable of emitting a white light by itself. The LED therefore cannot emit a white light by itself, and three methods as shown below, for example, are known as methods for generating a white light using an LED or LEDs as a light source:

(1) a method of using a blue LED as an LED, irradiating a fluorescent body with the light emitted from the blue LED to output a yellow light, and generating a white light by mixing the blue light emitted from the blue LED and the yellow light emitted from the fluorescent body;

(2) a method of using a near-ultraviolet LED as an LED, irradiating a plurality of kinds of fluorescent bodies with the light emitted from the near-ultraviolet LED to output lights of a plurality of colors, and generating a white light by mixing the outputted lights of the plurality of colors; and (3) a method of using a red LED, a green LED and a blue LED as LEDs, and generating a white light by mixing the red light emitted from the red LED, the green light emitted from the green LED and the blue light emitted from the blue LED.

Among the above-described methods, the methods (1) and (2) can be used only for simultaneous illumination for irradiating a subject with a white light itself. On the other hand, the method (3) can be used not only for simultaneous illumination but also for frame-sequential illumination in which the red light, the green light and the blue light are irradiated in a time-series manner.

When the method (3) among the methods is employed, color balance adjustment for bringing the light close to a purer white light by adjusting the ratio among the light emission intensities of the red LED, the green LED and the blue LED is performed as an adjustment at the time of factory shipment of a light source apparatus.

It is known that light emission intensities of LEDs change with the passage of time (change over ages). Description will be made on this point with reference to FIG. 4 related to the present application.

Figure 4:
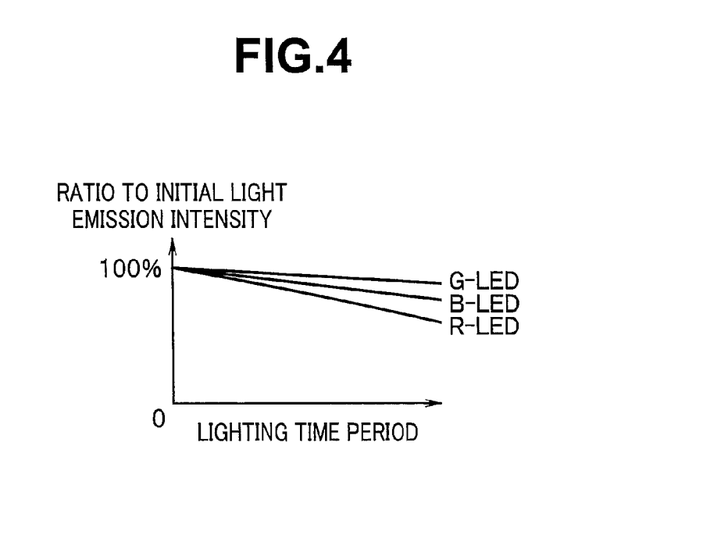
FIG. 4 is a diagrammatic view illustrating how the light emission intensities of the respective color LEDs in the light source apparatus change with the passage of time in the first embodiment.

As shown in FIG. 4, the light emission intensities of the respective color LEDs decrease with time, for example, and the decrease degree differs for each color.

Thus, even if the color balance adjustment is performed at the time of factory shipment, if no further measure is taken, the color balance changes with time.

A technology therefore has been proposed in which sensors for detecting the light emitting luminance of the respective color LEDs are provided and color balance is readjusted at an appropriate timing on the basis of detection results obtained by the sensors. However, if the sensors are fixedly arranged on the optical path of the illumination light, the light amount of the illumination light which reaches a subject is decreased.

In order to solve such a problem, for example, Japanese Patent Application Laid-Open Publication No. 2010-158415 discloses a technology for performing detection by using leak lights which are not used as an illumination light. In the technology recited in the publication, a red LED, a green LED and a blue LED are made to emit light in a frame-sequential manner first and the light emission intensity is measured by one light-receiving section, and color adjustment is performed such that the output voltage from the light-receiving section with respect to each color becomes a reference voltage value for each color according to the brightness set by a user (See paragraphs [0020]-[0028], FIG. 1, FIG. 2, etc.). In the technology, the reference voltage value for each color is calculated such that the light emission intensities of the red light, the green light and the blue light becomes a constant ratio (See paragraphs [0027], [0028], etc.). In addition, it is disclosed that the light emitted from each of the red LED, the green LED and the blue LED is received at the light-receiving section to acquire information on the emitted light amount, and the driving amount and also the emitted light amount of each of the red LED, the green LED and the blue LED are accurately adjusted, in view of variation of the emitted light amount due to a change over the ages and a temperature change (See paragraph [0050] etc.).

SUMMARY OF THE INVENTION

A light source apparatus according to one aspect of the present invention is a light source apparatus which generates a light to be supplied to an endoscope and includes: a light-emitting element that emits a light; an optical element that receives the light emitted from the light-emitting element and emits the received light; and a light emission intensity detection section that is arranged at a position where the light emission intensity detection section is able to receive both of a leak light of the light emitted from the light-emitting element, the leak light not being used as an illumination light, and a light emitted from the light-emitting element and reflected by the optical element.

DETAILED DESCRIPTION OF THE PREFERRED EMBODIMENT(S)

Hereinafter, embodiments of the present invention will be described with reference to drawings.

First Embodiment

Figure 1:
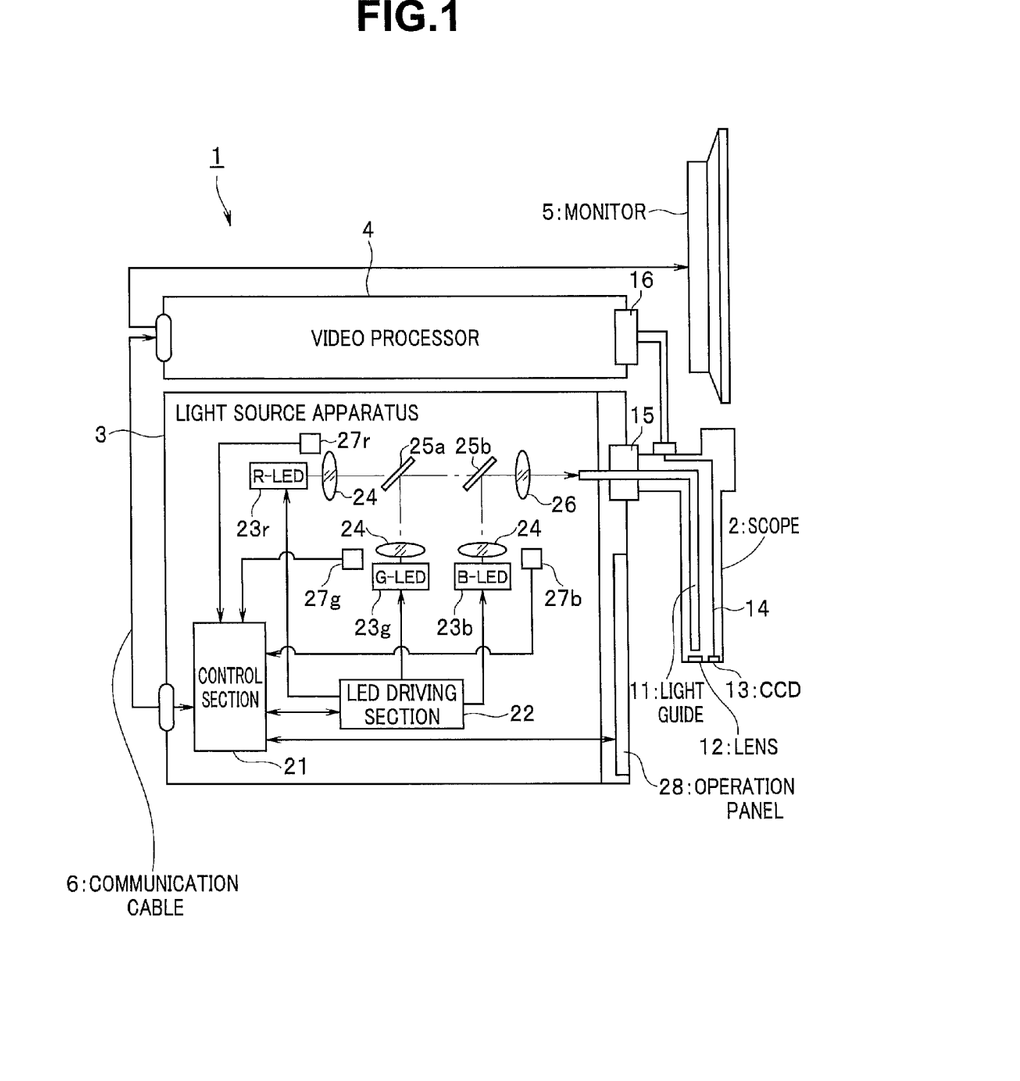
FIG. 1 illustrates a configuration of an endoscope system according to a first embodiment of the present invention.

FIGS. 1 to 12 illustrate the first embodiment of the present invention and FIG. 1 illustrates a configuration of an endoscope system.

An endoscope system 1 includes a scope 2, a light source apparatus 3, a video processor 4, a monitor 5, and a communication cable 6.

The light source apparatus 3 uses light-emitting elements of a plurality of colors as light sources, and the light-emitting elements of the plurality of colors include, for example, light-emitting elements for emitting lights of three colors which constitute a white light, and more specifically, a red LED (R-LED) 23r as a red (R) light-emitting element, a green LED (G-LED) 23g as a green (G) light-emitting element, and a blue LED (B-LED) 23b as a blue (B) light-emitting element, for example. The emission spectra of the respective light-emitting elements differ from one another, and as shown in FIG. 2, the light emitted from the red LED 23r has a spectrum in a band of red light R, the light emitted from the green LED 23g has a spectrum in a band of green light G, and the light emitted from the blue LED 23b has a spectrum in a band of blue light B.

Figure 2:
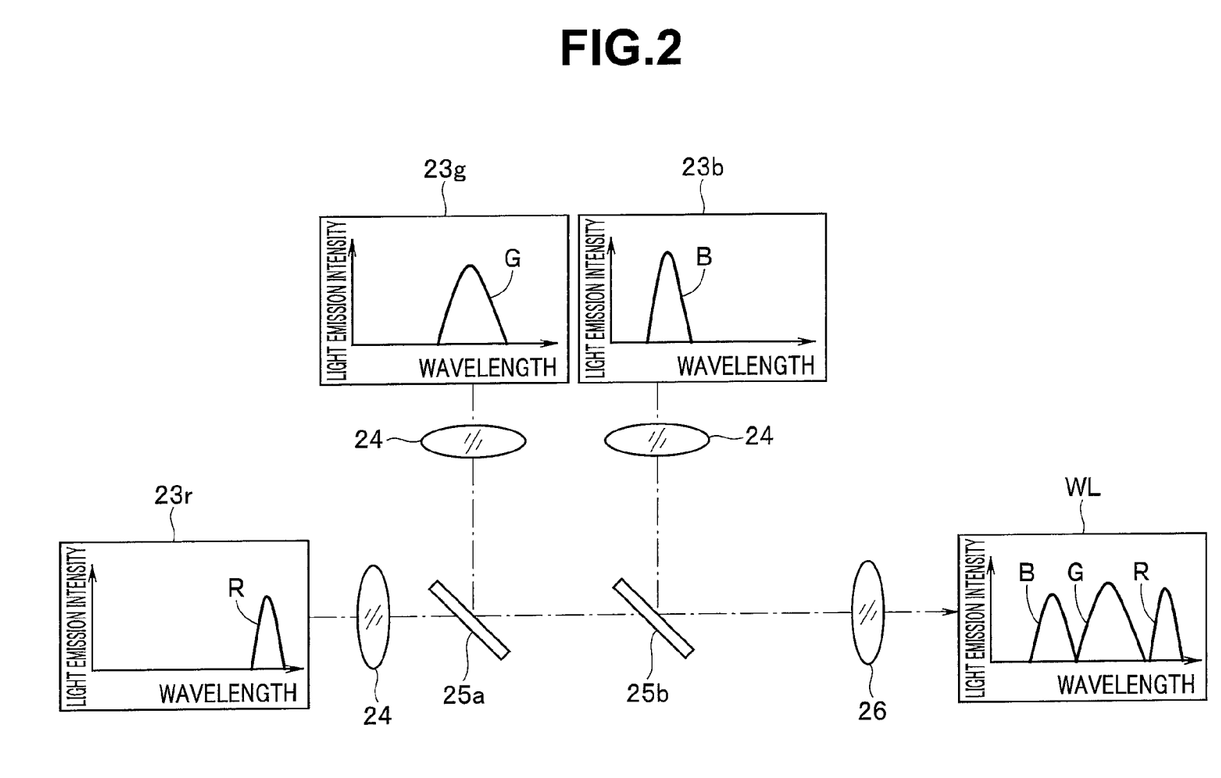
FIG. 2 illustrates an aspect of spectra of lights emitted from the respective color LEDs in a light source apparatus in the first embodiment.

FIG. 2 illustrates an aspect of the spectra of the lights emitted from the respective color LEDs in a light source apparatus.

An LED driving section 22 provided in the light source apparatus 3 is a light-emitting element driving section that drives the red LED 23r, the green LED 23g, and the blue LED 23b by respectively supplying currents to the LEDs.

A control section 21 provided in the light source apparatus 3 controls the currents supplied from the LED driving section 22, to thereby adjust the respective intensities of the emitted lights of the red LED 23r, the green LED 23g, and the blue LED 23b. The control by the control section 21 is performed on the basis of inputs from illuminance sensors 27r, 27g and 27b to be described later, brightness information of an object acquired by communicating with the video processor 4 through the communication cable 6, or brightness setting of the illumination light performed by a user through an operation panel 28.

The light source apparatus 3 is provided with three collimator lenses 24, two dichroic filters 25a, 25b, and one condensing lens 26, as an optical system that transmits the illumination light.

The three collimator lenses 24 are optical elements which are respectively disposed on the optical paths of the emission lights from the red LED 23r, the green LED 23g, and the blue LED 23b, and which emit the incident lights as parallel lights.

The first dichroic filter 25a is an optical element that transmits the red light R from the red LED 23r and reflects the green light G from the green LED 23g.

The second dichroic filter 25b is an optical element that transmits the red light R from the red LED 23r and the green light G from the green LED 23g, and reflects the blue light B from the blue LED 23b.

The condensing lens 26 is an optical element that condenses a parallel luminous flux from the second dichroic filter 25b onto an incident end face at the proximal end of a light guide 11 of the scope 2.

When the three light-emitting elements, that is, the red LED 23r, the green LED 23g and the blue LED 23b are made to emit lights at the same time, if the light emission intensities of the respective color LEDs are within a predetermined range, the light emitted from the condensing lens 26 becomes a white illumination light WL containing all the three colors of RGB, as shown in FIG. 2.

Furthermore, the light source apparatus 3 is provided with an illuminance sensor 27r that detects the light emission intensity of the red LED 23r, an illuminance sensor 27g that detects the light emission intensity of the green LED 23g, and an illuminance sensor 27b that detects the light emission intensity of the blue LED 23b, as light emission intensity detection sections that detect the light emission intensities of the light-emitting elements of a plurality of colors. The illuminance sensors 27r, 27g and 27b are configured as monochrome sensors, for example, and disposed at positions where the leak lights which do not reach the incident end face of the light guide 11 among the luminous fluxes emitted from the respective color LEDs 23r, 23g and 23b are detected, (positions at which the illumination light is not kicked) (in the present embodiment, in the vicinity of the respective color LEDs 23r, 23g, and 23b). Then, the illuminance sensors 27r, 27g and 27b output the results of the detection of the light intensities to the control section 21.

The control section 21 controls the LED driving section 22 to adjust the light emission luminance (brightness) on the basis of brightness information from the video processor 4 (or brightness of the illumination light set by the user), and controls the LED driving section 22 to adjust the color balance of the illumination light on the basis of the detection results from the illuminance sensors 27r, 27g and 27b.

In addition, the operation panel 28 provided to the light source apparatus 3 is used when the user performs operations with respect to the light source apparatus 3, and enables the user to perform on/off operation of a power source of the light source apparatus 3, setting operation of an observation mode, setting operation of the brightness of the illumination light, and the like. The observation mode inputted from the operation panel 28 is transmitted to the video processor 4 through the control section 21 and the communication cable 6, and image processing is performed according to the observation mode in the video processor 4.

The scope 2 as an endoscope which receives a supply of the illumination light from the light source apparatus 3 is provided with the light guide 11, a lens 12, a CCD 13, a signal line 14, a light guide connector 15, and a video connector 16.

The light guide 11 has a proximal end extended from the light guide connector 15, and when the light guide connector 15 is connected to the light source apparatus 3, the light from the above-described condensing lens 26 is condensed on the incident end face at the proximal end of the light guide 11.

The light guide 11 is inserted through the insertion portion of the scope 2 to reach the distal end portion, and emits the illumination light from an emission face at the distal end thereof. The lens 12 for illumination is disposed at the distal end of the scope 2 so as to be located on the optical path of the illumination light. The illumination light from the light source apparatus 3 transmitted through inside the light guide 11 is irradiated from the distal end of the insertion portion to the subject through the lens 12.

The optical image of the subject irradiated with the illumination light is captured through an objective lens, not shown, disposed at the distal end of the insertion portion of the scope 2 and the image is formed on the CCD 13 which is an image pickup device. The CCD 13 is a color image pickup device in which a color filter array and the like are disposed, or a monochrome image pickup device which receives a frame-sequential illumination light. The CCD 13 then performs image pickup operation in which the optical image of the subject is converted into an electric signal, and sends the electric signal through the signal line 14 to the video processor 4 to which the video connector 16 is connected.

The video processor 4 synchronizes the images of the respective colors received from the CCD 13 to generate a color image signal, and after performing image processing such as color balance adjustment, gamma conversion, color conversion, and the like on the generated image signal, the video processor 4 converts the signal format of the image signal into a signal format for displaying the image signal on the monitor 5, to output the image signal to the monitor 5, and thereby a color image of the object is displayed on the monitor 5.

In addition, the video processor 4 extracts luminance signals, for example, from the received images of the respective colors, and creates brightness information on the basis of the extracted luminance signals. The brightness information thus created by the video processor 4 is transmitted to the control section 21 of the light source apparatus 3 through a communication cable 6 which connects the video processor 4 and the light source apparatus 3.

The control section 21 controls the light emission intensities of the respective color LEDs 23r, 23g and 23b as described above through the LED driving section 22 on the basis of the received brightness information and the output values of the illuminance sensors 27r, 27g and 27b.

Figure 3:
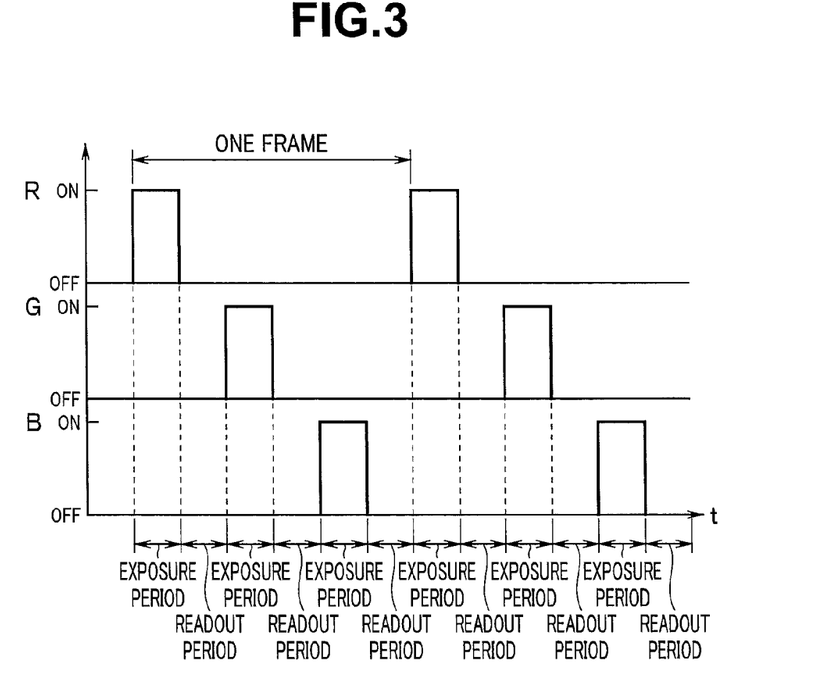
FIG. 3 is a timing chart showing light emitting timings of the respective color LEDs when frame-sequential illumination is performed in the first embodiment.

Next, FIG. 3 is a timing chart showing light emitting timings of the respective color LEDs when frame-sequential illumination is performed.

The CCD 13 alternately performs operation in an exposure period during which the CCD 13 receives a light to accumulate electric charges and operation in a readout period during which the accumulated electric charges are sequentially read out for each pixel.

In a case of the frame-sequential illumination, any one of the color LEDs is made to emit light during the exposure period to perform exposure, and all the LEDs are turned off during the readout period to read out exposure images. That is, in one-frame cycle operation, exposure is performed by making only the red LED 23r emit light, for example, in a certain exposure period and in the readout period after the certain exposure period, an R image obtained by exposing the red light R is read out, exposure is performed by making only the green LED 23g emit light in the next exposure period, and in the readout period after the next exposure period, a G image obtained by exposing the green light G is read out, and exposure is performed by making only the blue LED 23b emit light, for example, in the further next exposure period, and in the readout period after the further next exposure period, a B image obtained by exposing the blue light B is read out, and such one-frame cycle operation is repeatedly performed.

The frame-sequential illumination is described here as one example of the operation of the light source apparatus 3. However, detection of the light emission intensities of the respective color LEDs 23r, 23g and 23b by the illuminance sensors 27r, 27g and 27b as described below is not only performed in the frame-sequential illumination but also performed similarly in the simultaneous illumination.

Next, FIG. 4 is a diagrammatic view illustrating how the light emission intensities of the respective color LEDs in the light source apparatus 3 change with the passage of time.

It is known that the light emission intensities of LEDs change with the passage of time (degrade over ages). It is common that changes of the light intensities with the passage of time are different for each of the respective color LEDs 23r, 23g and 23b. FIG. 4 illustrates an example of the changes of the light emission intensities with the passage of time, when it is supposed that the initial light emission intensity of each of the color LEDs is 100% and the same amount of current as that at the time of initial light emission (for example, the maximum rating current) is supplied to each of the color LEDs.

In the example shown in FIG. 4, the light emission intensity of each of the color LEDs decreases with the passage of time. However, the decrease in the light emission intensity of the green LED 23g is the smallest, the decrease in the light emission intensity of the blue LED 23b is the second smallest, and the decrease in the light emission intensity of the red LED 23r is the largest.

Accordingly, the illuminance sensors 27r, 27g and 27b are provided to detect the light emission intensities of the respective color LEDs and the color balance and the light emission luminance (brightness) are controlled so as to be maintained based on the detection results, thereby addressing such changes of the light intensities.

Figure 5:
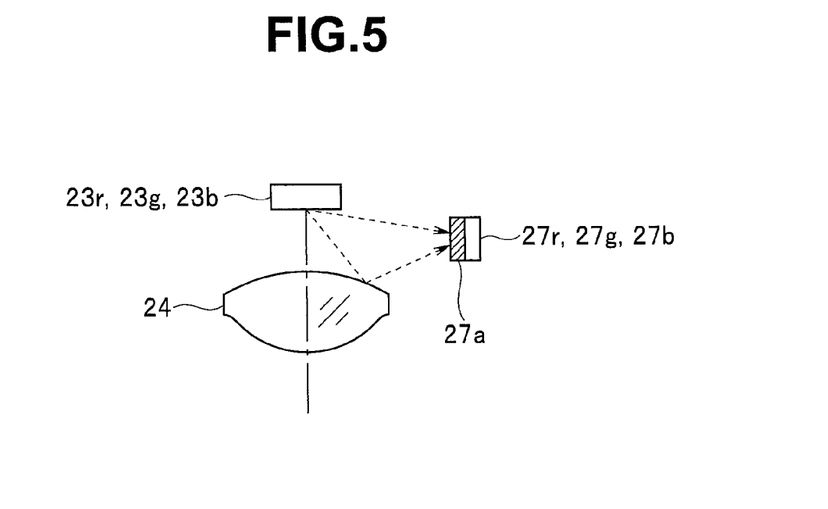
FIG. 5 illustrates an arrangement of illuminance sensors according to the first embodiment.

Next, FIG. 5 illustrates an arrangement of the illuminance sensors 27r, 27g and 27b.

In the present embodiment, the illuminance sensors 27r, 27g and 27b are arranged at positions where the sensors can receive the leak lights among the lights emitted from the respective color LEDs 23r, 23g and 23b, which are not used as the illumination light, and also can receive the lights emitted from the respective color LEDs 23r, 23g and 23b and reflected by the collimator lenses 24. In particular, as shown in FIG. 5, the illuminance sensors are arranged on a lateral side in the space between the respective color LEDs 23r, 23g and 23b and the collimator lenses 24.

Figure 6:
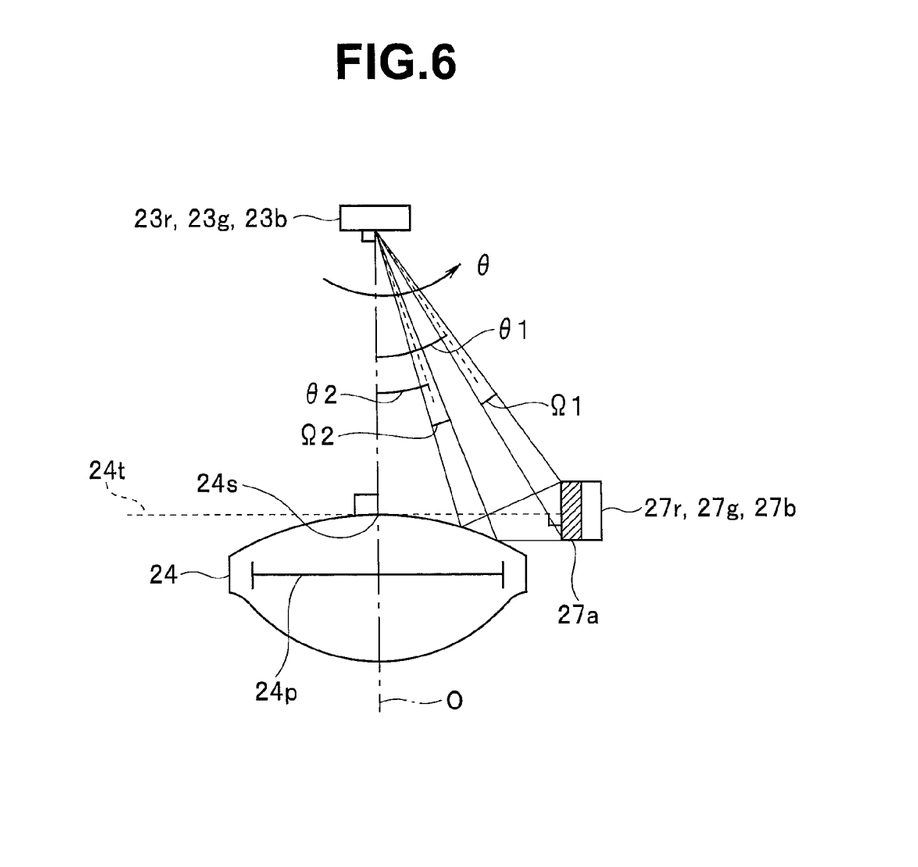
FIG. 6 illustrates an example of more detailed arrangement of the illuminance sensors according to the first embodiment.
Figure 7:
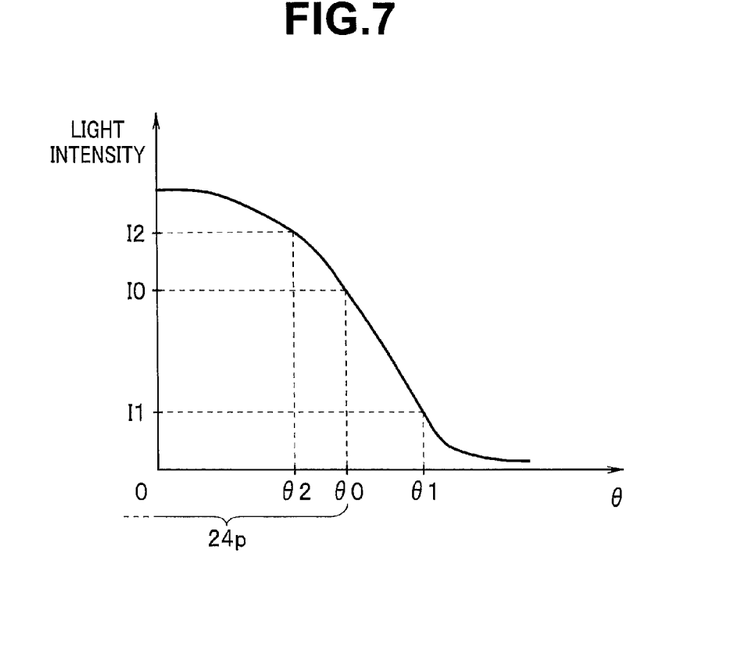
FIG. 7 is a diagrammatic view illustrating a relationship between light intensity distribution according to the emission directions of the lights emitted from the respective color LEDs and the arrangement of the illuminance sensors in the first embodiment.

FIG. 6 illustrates an example of more detailed arrangement of the illuminance sensors 27r, 27g and 27b, and FIG. 7 is a diagrammatic view illustrating a relationship between the light intensity distribution according to the emission directions of the lights emitted from the respective color LEDs 23r, 23g, and 23b and the arrangement of the illuminance sensors 27r, 27g and 27b.

As shown in FIG. 7, the intensity of the light emitted from each of the color LEDs 23r, 23g and 23b decreases as the emission angle θ (the optical axis direction is indicated by θ=0) shown in FIG. 6 becomes larger from the optical axis direction, with the optical axis direction connecting each of the color LEDs 23r, 23g and 23b and a principal point of each of the collimator lenses 24 as a peak. In addition, the light emitted from each of the color LEDs has a distribution in which the light (the emission angle of which is θ0 as shown in FIG. 7) which reaches the periphery of an entrance pupil 24p of each of the collimator lenses 24 maintains a certain degree of light intensity I0, but when the emission angle becomes larger than θ0, the light intensity rapidly decreases to be close to zero.

The solid angle of the leak light emitted from each of the color LEDs 23r, 23g and 23b and directly incident into each of the illuminance sensors 27r, 27g and 27b is defined as Ω1, and the solid angle of the light emitted from each of the color LEDs 23r, 23g and 23b and reflected by an incident surface of each of the collimator lenses 24 is defined as Ω2. Furthermore, if it is supposed that an angle of emergence at the center of the solid angle Ω1 is θ1 and an angle of emergence at the center of the solid angle Ω2 is θ2, the light intensity at the angle of emergence θ1 is I1 and the light intensity at the angle of emergence θ2 is I2, as shown in FIG. 7. In addition, if it is supposed that the reflection rate of the incident surface of each of the collimator lenses 24 with respect to the light beam having the angle of emergence θ2 is Ref, a light receiving intensity SI of the light received by each of the illuminance sensors 27r, 27g and 27b is calculated approximately, as expressed by the mathematical formula 1 shown below.

$$SI = \Omega1 \times I1 + \Omega2 \times I2 \times Ref + \alpha \quad \text{[Formula 1]}$$

In this formula, α represents the light intensity which is generated by other factors, for example, the lights which reach the illuminance sensors 27r, 27g and 27b after having been reflected inside the collimator lenses 24, internal reflection along the optical paths, return lights reflected from the optical elements located at further subsequent stages, or the like. The α is considered to contribute relatively less to the light receiving intensities of the illuminance sensors 27r, 27g and 27b, and in many cases, there is no problem in carrying out an approximation by ignoring the α.

Among the light intensity components shown in the formula 1, the first component (Ω1×I1) corresponds to the intensity component of the lights received in the conventional arrangement of the sensors. On the other hand, the second component (Ω2×I2×Ref) is the intensity component of the lights intended to be positively received in order to increase the light receiving intensity in the present invention. As understood from FIG. 7, since the leak lights at the angle of emergence θ1 are peripheral lights, the light intensity I1 is small. In contrast, since the lights at the angle of emergence θ2 are the lights to be originally used as the illumination light, the light intensity I2 is much greater than the light intensity I1. Thus, the contribution rate of the second component in the light receiving intensity SI cannot be ignored even if the reflection rate Ref is considerably small, and if the reflection rate is large to some extent, the contribution rate of the second component would be able to be on par with the contribution rate of the first component (or, if the illuminance sensors 27r, 27g and 27b are arranged at positions where all the reflected lights from the incident surfaces of the collimator lenses 24 are received, it can be considered that the second component will exceed the first component).

It is thus preferable that the illuminance sensors 27r, 27g and 27b are arranged at the positions in the vicinity of the outside of the respective entrance pupils 24p of the collimator lenses 24 where the light receiving intensity SI is the highest, more definitely, the positions where the light intensity of the lights obtained by adding up the leak lights (the first component) and the lights reflected by the collimator lenses 24 (the second component) is the highest. Such an arrangement is not limited to the one to be calculated theoretically, but may be calculated experimentally while changing the arrangement of the illuminance sensors 27r, 27g and 27b.

As an arrangement of the sensors in which not only the first component but also the second component can be effectively received, in the present embodiment, as shown in FIG. 6, each of the illuminance sensors 27r, 27g and 27b is disposed in the vicinity of the outside of the entrance pupil 24p of each of the collimator lenses 24 so as to be located on a contacting plane 24t contacting a surface top 24s of the incident surface of each of the collimator lenses 24 such that the light-receiving surface 27a is directed toward the surface top 24s (that is, the light-receiving surface 27a is directed in a direction vertical to the optical axis O).

The arrangement as shown in FIG. 6 provides such advantages that the first component and the second component can be received effectively and the arrangement can be designed easily.

However, the arrangement shown in FIG. 6 is one example, and it is preferable to optimize the arrangement also in view of factors other than those described above, e.g., the distances between the collimator lenses 24 and the respective color LEDs 23r, 23g and 23b, the curvature of the optical surfaces of the collimator lenses 24 (curvature of the incident surfaces, in particular), the refractive index of the glass material which forms the collimator lenses 24, or the above-described position range within which all the reflected lights can be received.

Figure 8:
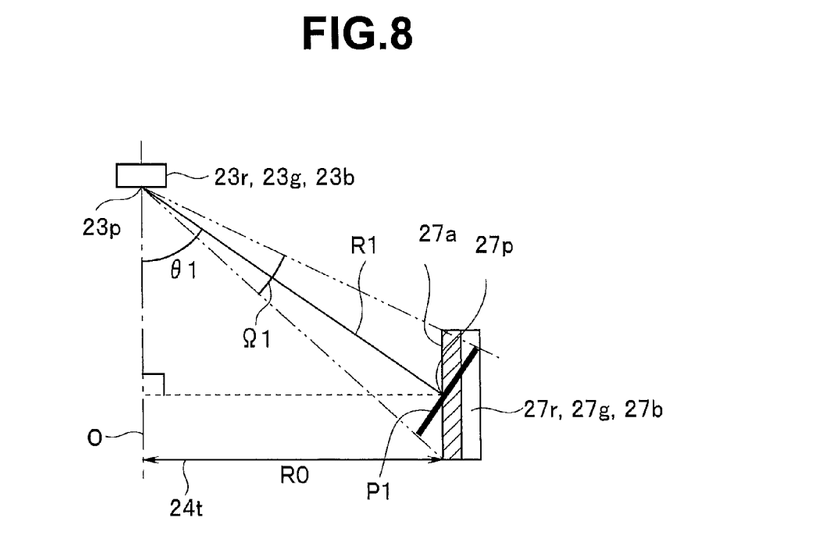
FIG. 8 illustrates a layout of the respective color LEDs and the illuminance sensors under a predetermined arrangement restriction in the first embodiment.

Next, with reference to FIGS. 8 and 9, description will be made on an arrangement in which the light-receiving performance is maximized when the illuminance sensors 27r, 27g and 27b receive the first component (Ω1×I1) under a predetermined arrangement restriction. FIG. 8 illustrates a layout of the respective color LEDs 23r, 23g and 23b and the illuminance sensors 27r, 27g and 27b under a predetermined arrangement restriction, and FIG. 9 is a diagrammatic view illustrating a light-receiving performance when the arrangement angles of the illuminance sensors 27r, 27g and 27g are changed with the respective color LEDs 23r, 23g and 23b as a center under the predetermined arrangement restriction.

In view of the configuration of a substrate to which each of the illuminance sensors 27r, 27g and 27b are mounted, a layout of other components, workability at the time when the substrate is assembled, a production cost, production accuracy, etc., it is not necessarily that the illuminance sensors 27r, 27g and 27b can be always arranged at the optimal positions, and there is a case where a certain level of arrangement restriction is imposed.

In the example shown in FIG. 8, it is supposed that an arrangement restriction is imposed on the arrangement of the illuminance sensors 27r, 27g and 27b, in which a normal line raised on each of the light-receiving surfaces 27a vertically intersects with the optical axis O connecting each of the respective color LEDs 23r, 23g and 23b and each of the collimator lenses 24. This arrangement restriction can be regarded as an arrangement restriction which satisfy the condition under which both of the above-described first component and second component can be received, since the illuminance sensors 27r, 27g and 27b can receive both of the leak lights from the respective color LEDs 23r, 23g and 23b and the reflected lights from the collimator lenses 24b.

Figure 9:
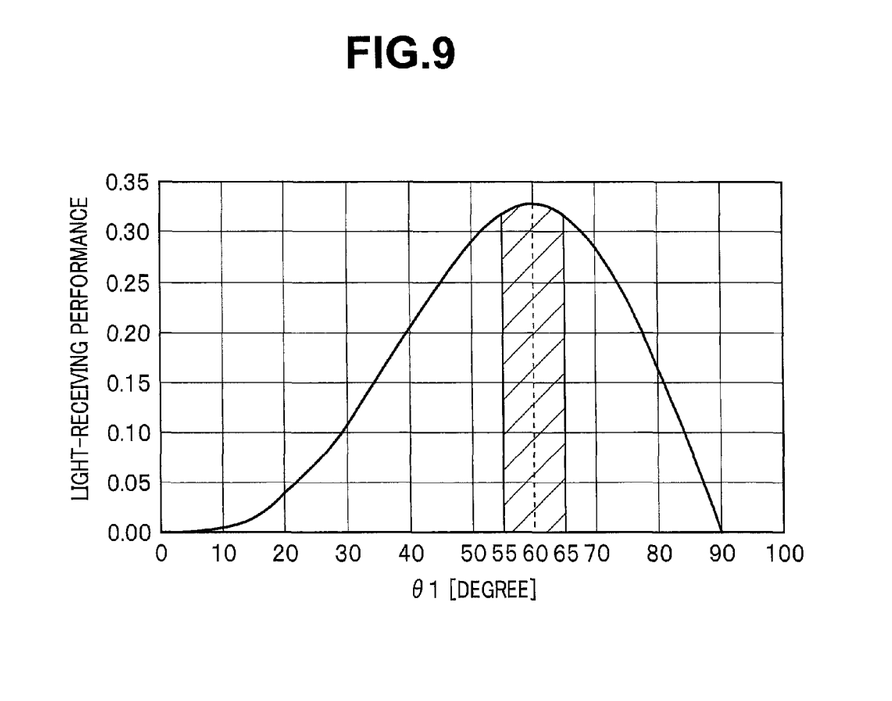
FIG. 9 is a diagrammatic view illustrating a light-receiving performance when the arrangement angle of the illuminance sensors are changed with the respective color LEDs as a center under the predetermined arrangement restriction in the first embodiment.

FIG. 9 is a diagrammatic view illustrating the light-receiving performance of the illuminance sensors 27r, 27g and 27b at the time when the angle of emergence θ1 is changed from 0 degree to 90 degrees under the arrangement restriction shown in FIG. 8. The angle of emergence θ1 is the angle formed by the center of the solid angle Ω1 with respect to the optical axis O as described above, and is also the angle formed by the line segment R1, which connects a center 27p of the light-receiving surface 27a of each of the illuminance sensors 27r, 27g and 27b and a center 23p of the light-emission surface of each of the color LEDs 23r, 23g and 23b, with respect to the optical axis O. In addition, the diagrammatic view shown in FIG. 9 illustrates how the light-receiving performance changes when the length of the line segment R1 is fixed and only the angle of emergence θ1 is changed. Note that the numerical values assigned to the axis of the light-receiving performance are the numerical values for indicating the relative scale of the light-receiving performance.

Under the above-described arrangement restriction, each of the light-receiving surfaces 27a is parallel to the optical axis O. Therefore, when the angle of emergence θ1 gets close to zero degree, also the solid angle Ω1 gets close to zero degree. That is, also an effective light-receiving area P1 at the time when each of the light-receiving surfaces 27a is viewed from each of the color LEDs 23r, 23g and 23b gets close to zero, as the angle of emergence θ1 gets close to zero, and the light-receiving performance of each of the illuminance sensors 27r, 27g and 27b gets close to zero as shown in FIG. 9.

On the other hand, if the angle of emergence θ1 gets close to 90 degrees, the effective light-receiving area P1 at the time when each of the light-receiving surfaces 27a is viewed from each of the color LEDs 23r, 23g and 23b gets close to a maximum value (that is, the area of each of the light-receiving surfaces 27a itself), but an effective light emitting area at the time when the light-emission surface of each of the color LEDs 23r, 23g and 23b is viewed from each of the light-receiving surfaces 27a gets close to zero. As a result, the intensity of the illumination light to be received gets close to zero. Accordingly, the light-receiving performance of the illuminance sensors 27r, 27g and 27b also get close to zero as shown in FIG. 9.

As shown in FIG. 9, the light-receiving performance of the illuminance sensors 27r, 27g and 27b reaches the local maximum value when θ1 is equal to 60 degrees. In view of some margin range (±5 degrees, for example), it is preferable to arrange the illuminance sensors 27r, 27g and 27b such that the angle of emergence θ1 is within the range from 55 degrees to 65 degrees (see the hatching part in FIG. 9).

As described above, it is necessary to arrange each of the illuminance sensors 27r, 27g and 27b outside the entrance pupil 24p of each of the collimator lenses 24 so as not to kick the illumination light, and for a practical purpose, each of the illuminance sensors has to be arranged outside the radius R0 (see FIG. 8) of each of the collimator lenses 24 (that is, outside the outer circumference of each of the collimator lenses 24). In addition, generally the illuminance is inversely proportional to the square of the distance from the light source. It is therefore preferable that the length of the line segment R1 is as short as possible. Furthermore, in order to effectively receive the reflected light from each of the condensing lenses 24 (the second component), it is preferable to arrange each of the illuminance sensors 27r, 27g and 27b in the vicinity of the incident surface of each of the collimator lenses 24.

It is FIG. 8 that illustrates an example of such an arrangement. The illuminance sensors 27r, 27g and 27b are arranged in the vicinity of the outside of the radius R0 of each of the collimator lenses 24 (note that the position illustrating the radius R0 in FIG. 8 is a position of the contacting plane 24t which contacts the surface top 24s of the incident surface of each of the collimator lenses 24, for example) such that the normal line of the light-receiving surface 27a is perpendicular to the optical axis O and the angle of emergence θ1 is approximately 60 degrees.

Figure 10:
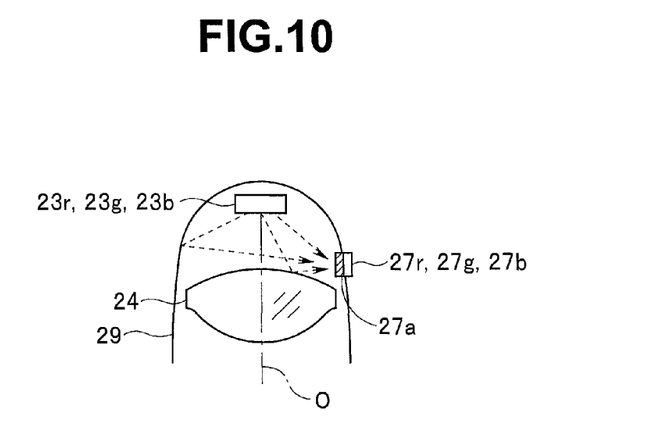
FIG. 10 illustrates a modified example of the arrangement of the illuminance sensors according to the first embodiment.

Furthermore, FIG. 10 illustrates a modified example of the arrangement of the illuminance sensors 27r, 27g and 27b.

As shown in FIG. 10, it is preferable to provide parabolic mirrors (reflectors) 29 with the optical axes as rotational symmetrical axes, for example, as reflective optical elements. In this case, each of the illuminance sensors 27r, 27g and 27b is arranged such that the light-receiving surface 27a is exposed in a reflection surface of each of the mirrors 29. If such a configuration is adopted, not only the lights which become leak lights in the case where the mirrors 29 are not provided can be effectively used as the illumination light, but also the light intensity of each of the lights incident on the illuminance sensors 27r, 27g and 27b can be increased, and color mixture due to the leak lights from adjacent LEDs is prevented (or reduced) and also a certain level of dust-proof effect can be obtained.

Figure 11:
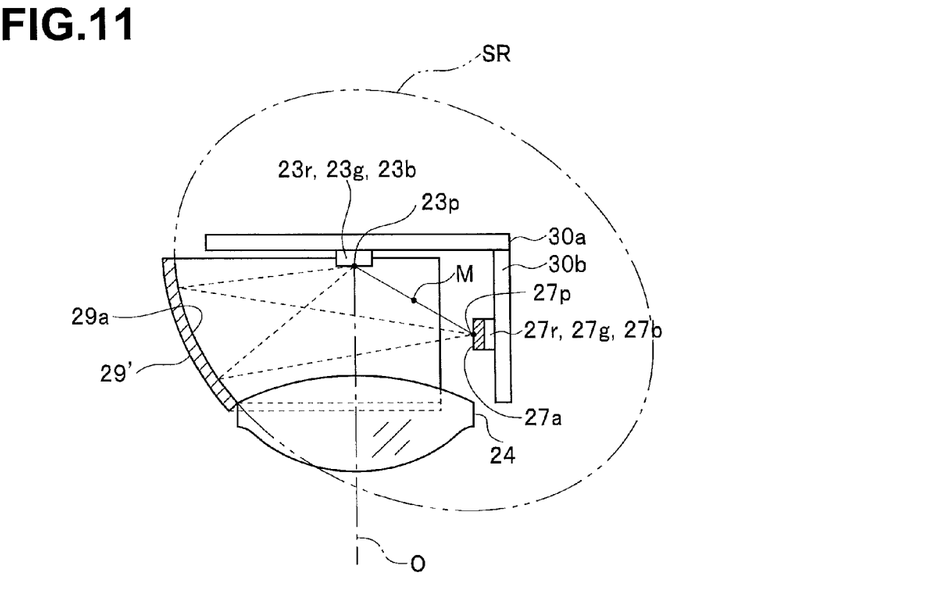
FIG. 11 illustrates an example in which a shape of a mirror is optimized for illuminance detection in the modified example of arrangement of the illuminance sensors in the first embodiment.

Alternatively, as a modified example of the configuration shown in FIG. 10, it can be considered that the reflective optical elements which reflect the leak lights are configured to condense the reflected lights to the illuminance sensors 27r, 27g and 27b. FIG. 11 illustrates an example in which the shape of each of the mirrors is optimized for illuminance detection in the modified example of the arrangement of the illuminance sensors 27r, 27g and 27b.

Each of the respective color LEDs 23r, 23g and 23b is mounted onto an LED substrate 30a at the surface opposite to the light-emission surface thereof, for example. In addition, each of the illuminance sensors 27r, 27g and 27b is mounted onto a sensor substrate 30b at the surface opposite to the light-receiving surface 27a thereof, for example.

Mirrors 29' are provided such that each mirror is located on the opposite side of each of the illuminance sensors 27r, 27g and 27b across the optical axis O connecting the center 23p of the light-emission surface of each of the color LEDs 23r, 23g and 23b and the principal point of each of the collimator lenses 24, within a predetermined angle range about the optical axes O. Each of the mirrors 29' is arranged within the predetermined angle range about the optical axis O so as to be located in a range within which the illumination light which reaches each of the collimator lenses 24 from each of the color LEDs 23r, 23g and 23b is not blocked (that is, outside the entrance pupil 24p of each of the collimator lenses 24) and so as to be close to the optical axis O as much as possible, in order to increase the condensing efficiency and reduce the size.

Each of the mirrors 29' has a mirror surface 29a, as a reflection surface, which is formed on a side opposed to each of the color LEDs 23r, 23g and 23b and which is an elliptical surface. The surface 29a, in more detail, is configured as a part of a rotational elliptical surface SR with the center 23p of the light-emission surface of each of the color LEDs 23r, 23g and 23b and the center 27p of the light-receiving surface 27a of each of the illuminance sensors 27r, 27g and 27b as two focal points, and with a linear line connecting the center 23p and the center 27p as a rotational symmetrical axis. Thus, the center of the mirror surface 29a which is the rotational elliptical surface SR is a middle point M between the center 23p and the center 27p.

According to the configuration as shown in FIG. 11, most of the leak lights emitted from each of the color LEDs 23r, 23g and 23b located at one of the focal points of the rotational elliptical surface SR to reach the mirror surface 29a are condensed on each of the illuminance sensors 27r, 27g and 27b located at the other of the focal points, thereby capable of increasing the light intensities of the incident lights onto each of the illuminance sensors 27r, 27g and 27b more effectively.

Figure 12:
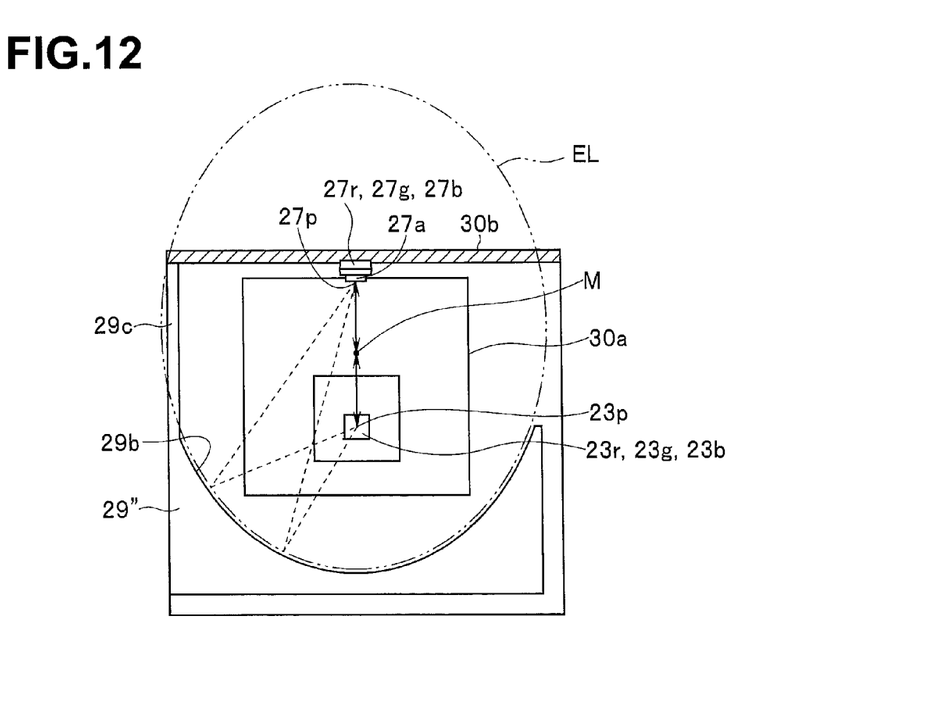
FIG. 12 illustrates a modified example of the example in which a shape of a mirror is optimized for illuminance detection in the modified example of arrangement of the illuminance sensors in the first embodiment.

FIG. 12 illustrates a modified example of the example in which the shape of each mirror is optimized for illuminance detection in the modified example of the arrangement of the illuminance sensors.

Also in the example shown in FIG. 12, similarly as in the example shown in FIG. 11, the reflective optical element which reflects the leak lights is configured to condense the reflected lights onto the illuminance sensors 27r, 27g and 27b. However, the shape of each mirror surface is more simplified.

That is, in the example shown in FIG. 11, since each of the mirror surfaces 29a has a shape which forms a part of the rotational elliptical surface SR, formation of the surface shape is complicated (for example, a surface shape which cannot be formed even if a plane is bent (non-Euclidean surface). In the present modified example, the shape of the mirror surface is simplified and formed in a surface shape which can be formed by bending a plane (Euclidean surface), for example.

The LED substrate 30a and the sensor substrate 30b are arranged such that the substrate surfaces are perpendicular to each other, for example, as shown in FIG. 12 (or also see FIG. 11), and the optical axis O and the substrate surface of the sensor substrate 30b are parallel to each other. Each mirror 29" in the present modified example has a mirror surface 29b configured as a part of an elliptic cylindrical surface EL with an axis, which passes through the middle point M between the center 23p of the light-emission surface of each of the color LEDs 23r, 23g and 23b and the center point 27p of the light-receiving surface 27a of each of the illuminance sensors 27r, 27g and 27b and which is parallel to the optical axis O, as a center.

Thus, the mirror surface 29b is configured such that the shape of the cross section vertical to the optical axis O forms a part of an ellipse, the focal points of which are located at the center 23p of the light-emission surface and the center 27p of the light-receiving surface 27a which are projected on the cross section. In addition, the distance between the center 23p and the middle point M, and the distance between the center 27p and the middle point M, which are projected on the cross section vertical to the optical axis O, are both the focal distances of the ellipse projected on the cross section.

Each of the above-described mirrors 29" and each of the sensor substrates 30b are arranged like a wall surrounding the optical axis O, thereby capable of preventing (or reducing) the color mixture due to the leak lights from the adjacent LEDs and obtaining a dust-proof effect to some extent.

Note that it is not necessary to surround the entire circumference of the optical axis O by each mirror 29" and each sensor substrate 30b. Therefore, a space exists between the mirror 29" and the sensor substrate 30b on the right side in FIG. 12. In addition, even if the mirror surface 29b of the mirror 29" is formed so as to have an elliptical cross section, there is a case where some part of the mirror surface 29b cannot obtain a high efficiency for reflecting the lights from each of the color LEDs 23r, 23g and 23b toward each of the illuminance sensors 27r, 27g and 27b. In the example shown in FIG. 12, the left side of the mirror 29" is formed as a linear wall portion 29c. Thus, the mirror surface 29b forms the elliptical cross section in a predetermined angle range about the optical axis O (in the example shown in FIG. 12, the angle range around 120 degrees, for example,) about the elliptical center (the point obtained by projecting the middle point M on the cross section vertical to the optical axis O).

According to the configuration shown in FIG. 12, an effect similar to that in the configuration shown in FIG. 11 can be achieved with the shape of the mirror surface 29b which can be produced more easily. As a result, the production cost is reduced and the productivity can be improved more than in the configuration shown in FIG. 11. In addition, as described above, also the color mixture prevention (reduction) effect and the dust-proof effect can also be obtained.

According to the first embodiment, the illuminance sensors 27r, 27g and 27b are arranged at the positions where both of the leak lights among the lights emitted from the respective color LEDs 23r, 23g and 23b, which are not used as the illumination light, and the lights emitted from the respective color LEDs 23r, 23g and 23b and reflected by the collimator lenses 24 can be received, thereby capable of detecting the light emission intensities under the lights having higher light emission intensities without reducing the light amount of the illumination light to be supplied to the scope 2 at all. As a result, it is possible to increase the detection efficiency and improve the detection accuracy.

Furthermore, when each of the illuminance sensors 27r, 27g and 27b is arranged such that the light-receiving surface 27a faces in a direction vertical to the optical axis, it is possible not only to effectively receive the lights but also to facilitate the design.

In addition, the mirrors 29 are provided, thereby capable of further improving the intensities of the lights to be received by the respective illuminance sensors 27r, 27g and 27b and obtaining the color mixture prevention (reduction) effect and the dust-proof effect. If the configuration including the mirror surface 29a as the rotational elliptical surface SR with two focal points at the center 23p of the light-emission surface of each of the color LEDs 23r, 23g and 23b and at the center 27p of the light-receiving surface 27a of each of the illuminance sensors 27r, 27g and 27b is adopted, the condensing rate of the leak lights can be optimized. On the other hand, the configuration including the mirror surface 29b as the elliptic cylindrical surface EL is adopted, it is possible to reduce the production cost and improve the productivity while obtaining the relatively high condensing rate of the leak lights.

Second Embodiment

Figure 13:
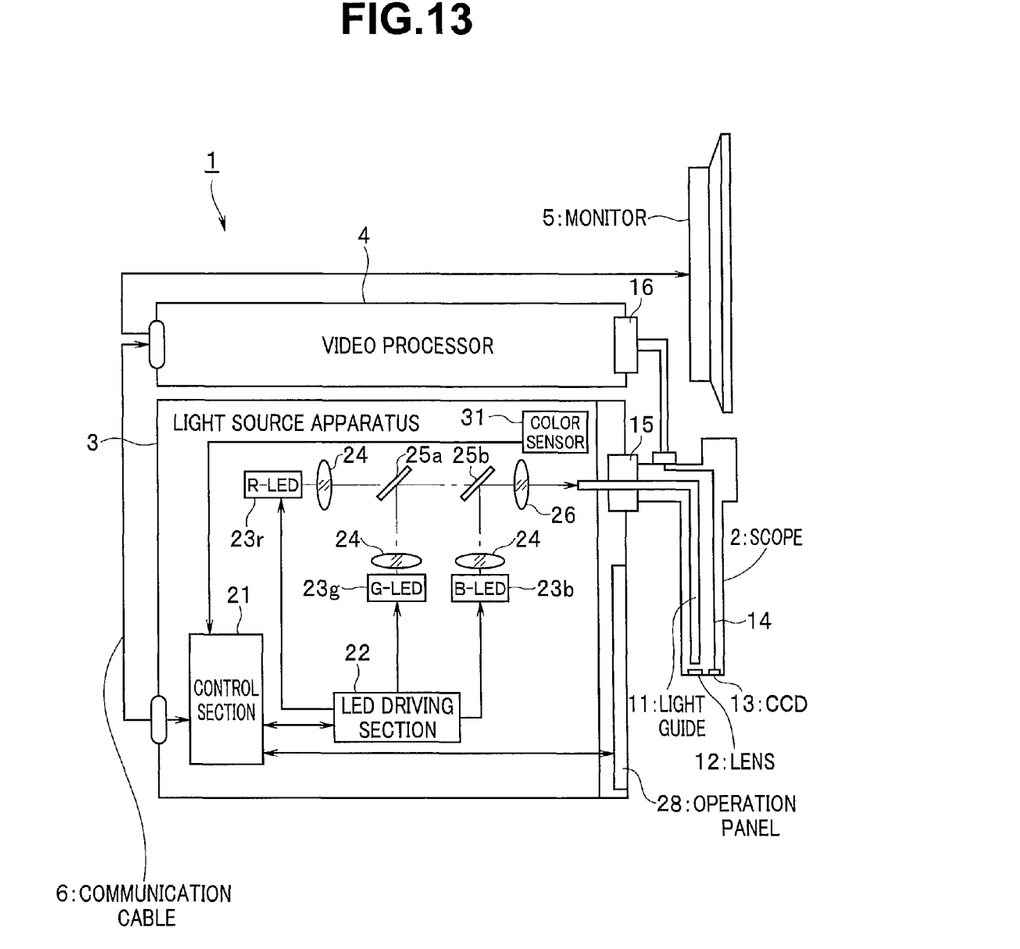
FIG. 13 illustrates a configuration of an endoscope system according to a second embodiment of the present invention.

FIGS. 13 to 17 illustrate the second embodiment of the present invention, and FIG. 13 illustrates a configuration of an endoscope system.

In the second embodiment, the similar parts as those in the first embodiment will be attached with the same reference numerals and descriptions thereof will be omitted. Only different points will be mainly described.

In the above-described first embodiment, the monochrome sensors are arranged in the vicinity of the respective color LEDs 23r, 23g and 23b. In the present embodiment, instead of the monochrome sensors, a color sensor is arranged at a position where any of the lights from the respective color LEDs 23r, 23g and 23b can be received.

Figure 14:
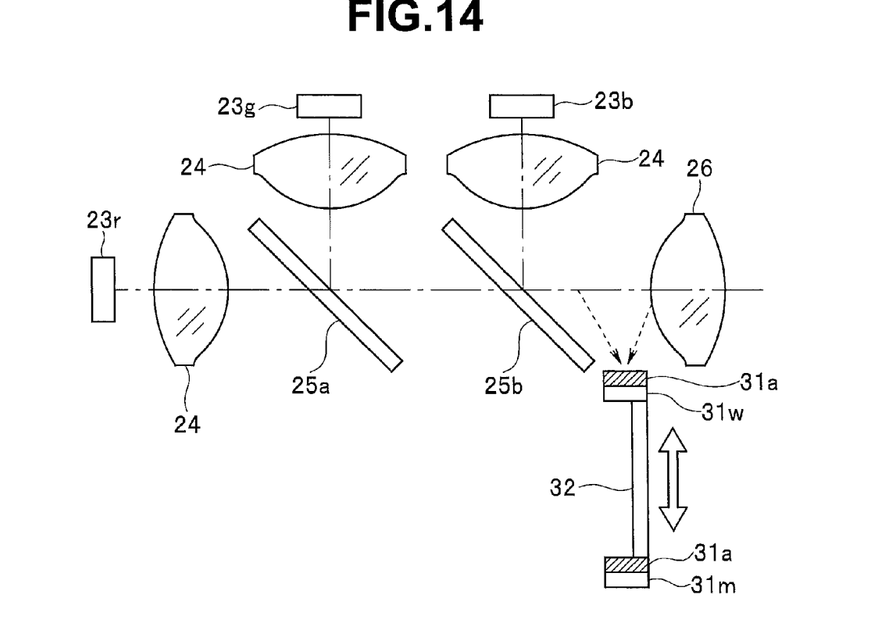
FIG. 14 illustrates an example in which a color sensor is arranged at a periphery of an optical filter provided insertably onto and removably from an optical path of an illumination light in the second embodiment.

That is, as shown in FIG. 13, the light source apparatus 3 is provide with a color sensor 31 that detects the light intensities of the red light R, the green light G and the blue light B by performing color sensing and outputs the detected light intensities to the control section 21. However, the color sensor 31, as will be described later with reference to FIG. 14, is configured by including a color sensor 31w for white light sensing and a sensor 31m for sensing lights in other observation modes.

The color sensor 31 is disposed at a position where the leak lights which do not reach the incident end face of the light guide 11 among the luminous flux emitted from the second dichroic filter 25b are detected, and in the present embodiment, disposed at a filter optical element which can be moved to a position between the second dichroic filter 25b and the condensing lens 26, for example.

The specific arrangement of the color sensor 31 is described with reference to FIG. 14. FIG. 14 illustrates an example in which the color sensor 31 is disposed at the periphery of the optical filter 32 (for example, at the part of the filter stand holding the optical filter 32) which is a filter optical element provided so as to be insertably onto and removably from the optical path of the illumination light.

The light source apparatus 3 in the present embodiment is provided with the optical filter 32 which is provided so as to be insertable into and removable from a position between the second dichroic lens 25b and the condensing lens 26. Note that the optical filter 32 is arranged between the second dichroic filter 25b and the condensing lens 26. However, the optical filter 32 may be arranged on the emission side of the condensing lens 26.

The optical filter 32 is moved according to the observation mode. When the endoscope system 1 is set in the white light observation mode, the optical filter 32 is retracted from the optical path of the illumination light (FIG. 14 shows an example in which the optical filter 32 is retracted downward from the optical path).

In addition, when the endoscope system 1 is set in another observation mode (for example, narrow-band light observation mode, fluorescent light observation mode, ultraviolet light observation mode, infrared light observation mode, or the like) other than the white light observation mode, the optical filter 32 is inserted onto the optical path of the illumination light. Though not shown in FIGS. 13 to 15, an LED with a light emission band other than RGB may be further provided.

In such a configuration, the color sensor 31w for white light sensing is disposed at the upper side periphery of the optical filter 32 such that the light-receiving surface 31a is directed upward (that is, toward the optical path direction of the illumination light). In addition, the sensor 31m (note that sensor 31m is a color sensor in some cases, and the sensor 31m is a monochrome sensor in other cases, according to the observation mode) for sensing the light in another observation mode is disposed at the lower side periphery of the optical filter 32 such that the light-receiving surface 31a is similarly directed upward. That is, the color sensor 31w and the sensor 31m are moved integrally with the optical filter 32.

According to such an arrangement, in the white light observation mode, the color sensor 31w for white light sensing receives both of the leak lights (first component) among the lights emitted from the respective color LEDs 23r, 23g and 23b, which are not used as the illumination light, and the lights (second component) emitted from the respective color LEDs 23r, 23g and 23b and reflected by the condensing lens 26.

Furthermore, in the other observation mode, the sensor 31m receives both the leak lights (first component) among the lights emitted from the respective color LEDs 23r, 23g and 23b (or LED provided in accordance with the other observation mode as described above), which are not used as the illumination light, and the lights (second component) emitted from the respective color LEDs 23r, 23g and 23b and reflected by the condensing lens 26.

Figure 15:
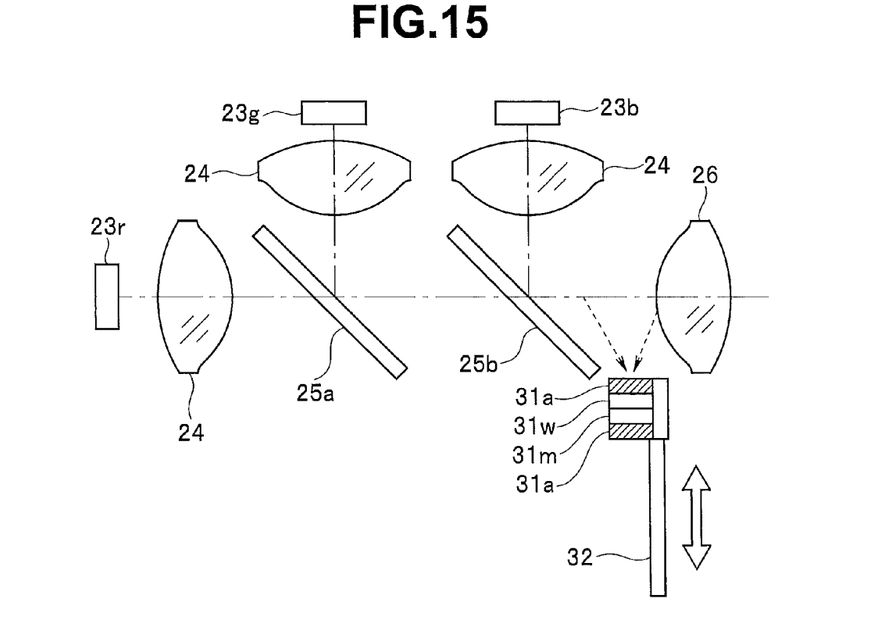
FIG. 15 illustrates another example in which the color sensor is arranged at the periphery of the optical filter provided insertably onto and removably from the optical path of the illumination light in the second embodiment.

In addition, FIG. 15 illustrates another example in which the color sensor 31 is disposed at the periphery of the optical filter 32 which is provided insertably onto and removably from the optical path of the illumination light.

In the exemplary configuration shown in FIG. 15, the sensor 31m for sensing the light in another observation mode is provided at the upper side periphery of the optical filter 32 such that the light-receiving surface 31a is directed downward, and on the sensor 31m, the color sensor 31w for white light sensing is further disposed such that the light-receiving surface 31a is directed upward.

Also according to such a configuration, it is possible to provide workings and effects which are substantially the same as those in the configuration shown in FIG. 14.

Note that the color sensor 31 is arranged in the vicinity of the condensing lens 26 in the present embodiment. However, in addition to the color sensor 31, a monochrome sensor as a second light emission intensity detection section may be arranged on the non-optical surface (peripheral surface, side surface, or the like which are not used as an optical surface related to the illumination light) of one or more collimator lenses 24.

Figure 16:
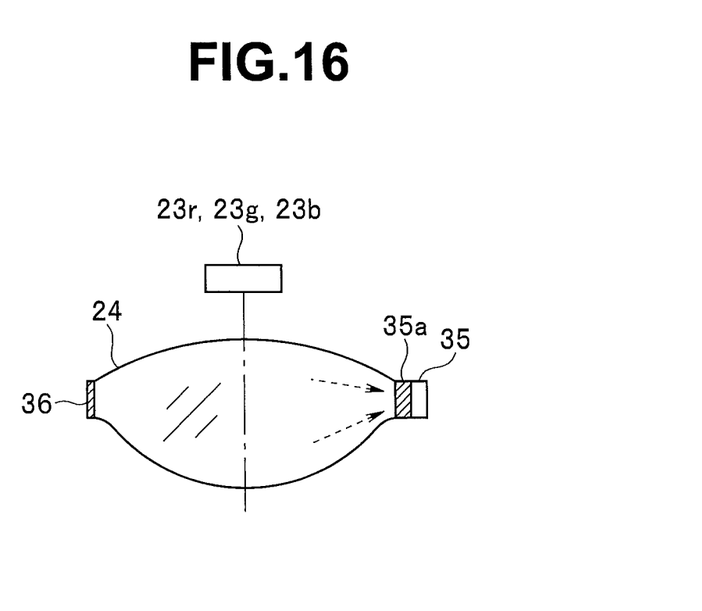
FIG. 16 illustrates an example in which a monochrome sensor is additionally arranged in the second embodiment.

FIG. 16 illustrates an example in which a monochrome sensor 35 is additionally arranged.

In the example shown in FIG. 16, the monochrome sensor 35 is provided such that the light-receiving surface 35a of the monochrome sensor 35 is located on the peripheral surface of the collimator lens 24 (that is, the light-receiving surface 35a is directed toward the inner side of the collimator lens 24). In addition, an internal reflection coating 36 that reflects lights into the collimator lens 24 is provided on a part of the peripheral surface of the collimator lens 24, the part being a region other than the region where the light-receiving surface 35a is arranged. Such a configuration enables the monochrome sensor 35 to receive diffusion lights in the collimator lens 24.

In addition, it is possible to increase the light intensity of the scattering light to be received by the monochrome sensor 35 by providing the internal reflection coating 36.

Figure 17:
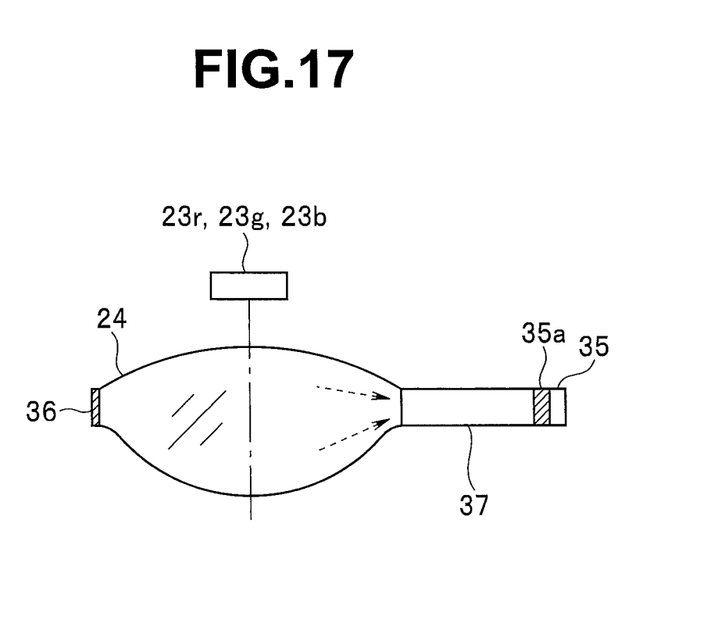
FIG. 17 illustrates another example in which the monochrome sensor is additionally arranged in the second embodiment.

In addition, FIG. 17 illustrates another example in which the monochrome sensor 35 is additionally arranged.

In the example shown in FIG. 17, a rod-like light guiding section 37 is added between the peripheral surface of the collimator lens 24 and the monochrome sensor 35. If such a configuration is adopted, there is an advantage that a degree of freedom of the arrangement of the monochrome sensor 35 is increased.

Note that FIGS. 16 and 17 describe the configuration in which the lights for detection are collected from the peripheral surface of the collimator lens 24. However, a configuration in which the lights for detection are collected from the non-optical surface of other optical elements such as other lenses or optical filters may be adopted.

Also the configurations shown in FIGS. 16 and 17 have an advantage that light emission intensity can be detected without decreasing the light amount of the illumination light.

According to the second embodiment thus configured, the color sensor 31 can receive both of the leak lights which are not used as the illumination light and the lights reflected by the optical element such as condensing lens 26, thereby capable of providing substantially the same effects as those in the above-described first embodiment.

In addition, by attaching the color sensor 31 to the filter optical element which is inserted onto and removed from the optical path of the illumination light according to the observation mode, when the observation mode is changed, it is possible to perform sensing with high detection efficiency and high detection accuracy using a sensor suitable for the observation mode.

Note that, regarding the reflected lights among the leak lights (first component) and the reflected lights (second component) which are received by the sensor or sensors, the reflected lights from the collimator lenses 24 are taken as the example in the first embodiment and the reflected lights from the condensing lens 26 are taken as the example in the second embodiment, respectively. However, the reflected lights are not limited to the above-described reflected lights, and may be reflected lights from any of the optical elements disposed on the optical path of the illumination light.

Note that the present invention is not limited to the above-described embodiments as they are, but can be embodied by modifying constituent elements without departing from the gist of the invention in the practical stage. In addition, various aspects of the invention can be formed by appropriately combining a plurality of constituent elements disclosed in the above-described embodiments. For example, some constituent elements may be deleted from all of the constituent elements shown in the embodiments. Furthermore, constituent elements in different embodiments may be appropriately combined. It is thus needless to say that various modifications and applications are possible without departing from the gist of the invention.

What is claimed is:

1. A light source apparatus which generates a light to be supplied to an endoscope, comprising:
    a light-emitting element that emits a light;
    an optical element that receives the light emitted from the light-emitting element and emits the received light; and
    a light emission intensity detection section that is arranged at a position where the light emission intensity detection section is able to receive both of a leak light of the light emitted from the light-emitting element, the leak light not being used as an illumination light, and a light emitted from the light-emitting element and reflected by the optical element.

2. The light source apparatus according to claim 1, wherein the optical element is a lens, and the light emission intensity detection section is arranged in a vicinity of an outside of an entrance pupil of the lens.

3. The light source apparatus according to claim 2, wherein the light emission intensity detection section is arranged in the vicinity of the outside of the entrance pupil of the lens so as to be located at a position where an intensity of a light obtained by adding up the leak light and the light reflected by the lens is the highest.

4. The light source apparatus according to claim 2, wherein the light emission intensity detection section is disposed on a plane contacting a surface top of an incident surface of the lens such that a light-receiving surface is directed to the surface top.

5. The light source apparatus according to claim 1, further comprising a reflective optical element that reflects the leak light of the light emitted from the light-emitting element, the leak light being not used as the illumination light, toward the light emission intensity detection section.

6. The light source apparatus according to claim 5, wherein the reflective optical element includes a reflection surface as a rotational elliptical surface with a position of the light-emitting element and a position of the light emission intensity detection section as focal points.

7. The light source apparatus according to claim 5, wherein the reflective optical element is configured such that a shape of a cross section vertical to an optical axis of the light-emitting element forms a part of an ellipse with a center of the light-emitting element and a center of the light emission intensity detection section as focal points, the centers being projected on the cross section.

8. The light source apparatus according to claim 2, wherein the lens is a collimator lens that receives the light emitted from the light-emitting element and emits the received light as a parallel light.

9. The light source apparatus according to claim 2, wherein the lens is a condensing lens that condenses the light emitted from the light-emitting element on an incident end face of a light guide of the endoscope.

10. The light source apparatus according to claim 1, wherein the light source device is capable of being switched among a plurality of observation modes,
    the light source apparatus further includes a filter optical element that is inserted onto and removed from an optical path of the illumination light according to the plurality of observation modes, and
    the light emission intensity detection section is moved together with the filter optical element.

11. The light source apparatus according to claim 10, wherein the light emission intensity detection section is provided in plurality in correspondence with the plurality of observation modes which correspond to insertion and removal of the filter optical element.

12. The light source apparatus according to claim 1, further comprising a second light emission intensity detection section that receives a scattering light inside the optical element from a non-optical surface of the optical element.

13. The light source apparatus according to claim 12, wherein an internal reflection coating is further provided on the non-optical surface of the optical element at a part other than a light-receiving part of the second light emission intensity detection section.

* * * * *